United States Patent [19]

Jackson et al.

[11] Patent Number: 4,906,402
[45] Date of Patent: Mar. 6, 1990

[54] LIQUID CRYSTAL MATERIAL

[75] Inventors: David A. Jackson, Radcliffe; Peter A. Gemmell, Runcorn Cheshire, both of United Kingdom

[73] Assignee: Imperial Chemical Industries, PLC, London, United Kingdom

[21] Appl. No.: 91,895

[22] Filed: Sep. 1, 1987

[30] Foreign Application Priority Data

Sep. 9, 1986 [GB] United Kingdom ............... 8621689

[51] Int. Cl.$^4$ ................. C09K 19/12; C09K 19/52; C07C 69/76; C07C 149/40
[52] U.S. Cl. .................. 252/299.65; 252/299.01; 252/299.66; 252/299.61; 252/299.62; 252/299.64; 252/299.67; 252/299.68; 350/350.5; 560/17; 560/18; 560/59; 560/61; 560/102; 558/257
[58] Field of Search ............ 252/299.01, 299.61, 252/299.62, 299.63, 299.64, 299.65, 299.66, 299.67, 299.68; 350/350.5; 558/257; 560/17, 18, 59, 61

[56] References Cited

U.S. PATENT DOCUMENTS

| 4,556,727 | 12/1985 | Walba | 252/299.67 |
|---|---|---|---|
| 4,561,726 | 12/1985 | Goodby et al. | 350/341 |
| 4,650,600 | 3/1987 | Hepphe et al. | 252/299.01 |
| 4,665,212 | 5/1987 | Makino et al. | 560/61 |
| 4,744,918 | 5/1988 | Hepphe et al. | 252/299.61 |

FOREIGN PATENT DOCUMENTS

| 0001804 | 5/1979 | European Pat. Off. |  |
|---|---|---|---|
| 0092181 | 10/1983 | . |  |
| 0123181 | 10/1984 | European Pat. Off. |  |
| 131373 | 1/1985 | European Pat. Off. |  |
| 136725 | 4/1985 | European Pat. Off. |  |
| 175591 | 3/1986 | European Pat. Off. |  |
| 2715184 | 10/1977 | Fed. Rep. of Germany |  |
| 3525015 | 1/1986 | Fed. Rep. of Germany |  |
| 219477 | 3/1985 | German Democratic Rep. |  |
| 6122051 | of 0000 | Japan |  |
| 62-198647 | 9/1987 | Japan | 252/299.65 |
| 87/198647 | 9/1987 | Japan | 252/299.65 |
| 430700 | 8/1967 | Switzerland |  |
| 2166754 | 5/1986 | United Kingdom |  |
| 86/02937 | 5/1986 | World Int. Prop. O. | 252/299.66 |
| 87/05012 | 8/1987 | World Int. Prop. O. |  |
| 87/05018 | 8/1987 | World Int. Prop. O. | 252/299.61 |
| 88/03525 | 5/1988 | World Int. Prop. O. |  |

OTHER PUBLICATIONS

Azzolina et al., CA 103: 160178n (1985).
European Search Report, Application No. EP 87307355.5.
Patent Abstract of Japan, vol. 10, No. 172, Jun. 18, 1986. The Patent Office Japanese Government, p. 85 C 354.

*Primary Examiner*—John F. Terapane
*Assistant Examiner*—J. E. Thomas
*Attorney, Agent, or Firm*—Cushman, Darby & Cushman

[57] ABSTRACT

A compound having ferroelectric liquid crystal properties of the formula:

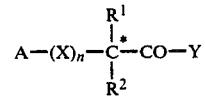

wherein
A is the residue of a liquid crystal material or a liquid crystal compatible material;
X is O or S;
n is 0 or 1;
Y is any inert group which does not cause the melting point of the compound of Formula I to exceed 200° C.;
$R^1$ is selected from H, $C_{1-4}$-alkyl and halogen; and
$R^2$ is $C_{1-4}$-alkyl or halogen;
provided that $R^1$ and $R^2$ are different. In a suitable environment the compound is capable of alignment in two metastable states and is therefore suitable for use in multiplex-addressed, liquid crystal devices, such as flat bed large area screens and displays.

15 Claims, No Drawings

LIQUID CRYSTAL MATERIAL

This specification describes an invention relating to a novel compound having ferro-electric properties and its use in liquid crystal applications.

According to the present invention there is provided a compound of the formula:

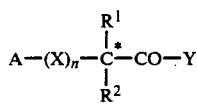

wherein
A is the residue of a liquid crystal material or a liquid crystal compatible material;
X is O or S;
n is 0 or 1;
Y is any inert group which does not cause the melting point of the compound of Formula I to exceed 200° C.;
$R^1$ is selected from H, $C_{1-4}$-alkyl and halogen; and
$R^2$ is $C_{1-4}$-alkyl or halogen;
provided that $R^1$ and $R^2$ are different.

The residue of the liquid crystal, or liquid crystal compatible, material represented by A is preferably of the formula:

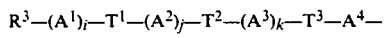

wherein
$R^3$ is selected from H, alkyl, alkoxy, alkylthio, fluoroalkyl & alkoxy, alkoxyalkyl, halogeno, alkyl- carbonyl & carbonyloxy and alkoxy- carbonyl & carbonyloxy;
$T^1$, $T^2$ & $T^3$ are independently selected from a single covalent bond or a group selected from —CO.O—, —O.CO—, —CO.S—, CS.O—, —CH=CH—, —CH$_2$O—, —OCH$_2$—, —N=N—,

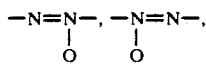

—N=CH—, —CH=N—, —CH$_2$CHD—, and —CHDCH$_2$—;
D is selected from H, cyano, halogen, CF$_3$ and CH$_3$;
$A^1$, $A^2$, $A^3$ & $A^4$ are independently selected from: optionally substituted 1,4-phenylene, optionally substituted 1,4-cyclohexylene optionally with one or two cyclic carbon atoms replaced by O or S, 1,4-bicyclo(2,2,2)octane, or 1,6-naphthylene or 1,4-naphthylene; and
i, j & k independently represent 0 or 1.

Where $R^3$ is other than H it preferably contains from 4 to 12, more preferably from 5 to 12, and especially from 6 to 12, carbon atoms. Preferred groups represented by $R^3$ are $C_{5-12}$-alkyl and $C_{5-12}$-alkoxy and more especially such groups containing at least 6 carbon atons.

It is preferred that each of $T^1$ to $T^3$ is independently selected from —CH$_2$.CH$_2$—, —O.CH$_2$—, —CH$_2$.O—, —O.CO— and more especially from —CO.O—, —CO.S— and a single covalent bond.

It is preferred that D is H but, where D is halogen, this is preferably selected from F, Cl and Br.

Where any one of $A^1$ to $A^4$ represents a substituted 1,4-phenylene group, it may contain up to 4 substituents selected from CH$_3$, OCH$_3$, CF$_3$, CN, NO$_2$, F, Cl, Br, OH and COCH$_3$ in the 2, 3, 5 and/or 6 positions in order to modify the physical properties of the molecule, e.g. melting point. It is however, preferred that the group is unsubstituted or substituted with a halogen, preferably F.

Where any one of $A^1$ to $A^4$ represents cyclohex-1,4-ylene optionally having one or two cyclic carbon atoms replaced by O or S it is desirably in the trans-configuration and preferably trans-1,3-dioxylene, especially trans-1,3-diox-2,5-ylene.

Where any one of $A^1$ to $A^4$ represents 1,4-cyclohexylene having one or more substituents, the substituents are preferably in the 1 and/or 4 positions, such as 1-cyanocyclohex-1,4-ylene.

It is preferred that the sum of i, j and k is 1, 2 or 3 and further preferred that two of i, j and k are 1.

It is preferred that X is O or S and more especially O.

It is preferred that $R^1$ is H or $C_{1-4}$-alkyl, especially H or CH$_3$, and that $R^2$ is $C_{1-4}$-alkyl, especially CH$_3$. It is especially preferred that $R^1$ is H and $R^2$ is CH$_3$. It is also preferred that not more than one of $R^1$ and $R^2$ is halogen, preferably F, Cl or Br.

The precise nature of the group represented by Y is not important provided it does not cause the compound of Formula I to have a melting point above 200° C., preferably not above 150° C., and more preferably not above 100° C. It is preferred that the compound of Formula I has a melting point of 50° C. or below and more preferably of 20° C. or below and that Y is selected to accord with this preference.

It is also preferred that Y does not represent or contain a group which has a strong tendency to form hydrogen bonds, such as OH and primary or secondary amino. Examples of suitable groups represented by Y are alkoxy, alkylthio, aryloxy, arylthio, alkyl, aryl, dialkylamino and H, in which the alkyl groups are linear, branched or cyclic or a combination of these. The aryl groups represented by or contained in Y are preferably phenyl or naphthyl and may be substituted by any of the substituents mentioned above for $A^1$ to $A^4$, other than those having a strong tendency to form hydrogen bonds, but especially preferred substituents are CN, halogen, alkyl and alkoxy. The alkyl groups represented by or contained in Y are preferably linear or branched $C_{1-20}$-alkyl, especially $C_{1-12}$-alkyl and more especially $C_{4-12}$-alkyl, or mono- or bi-$C_{4-12}$-cycloalkyl. The alkyl groups are optionally interrupted by O or S. It is especially preferred that Y is $C_{4-12}$-alkoxy.

A preferred compound according to the present invention conforms to the formula:

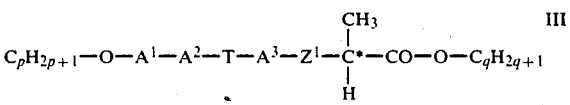

wherein
p is an integer from 6 to 12, especially from 7 to 12;
q is an integer from 2 to 12, especially from 5 to 10
$Z^1$ is O or S
T is —CO.O— or —CO.S—; and
$A^1$, $A^2$ & $A^3$ are each independently selected from 1,4-phenylene, 1,4-cyclohexylene, 1,4-cyclohexylene with one or two cyclic carbon atoms replaced by O or S, 1,4-bicyclo-(2,2,2)octane, 1,6-naphthylene and 1,4- naphthylene, either unsubstituted or carrying a fluoro substituent.

The terminal alkyl groups in the compound of Formula III may be linear, i.e. of the formulae $CH_3-(CH_2)_{p-1}-$ and $-(CH_2)_{q-1}-CH_3$, or branched.

Specific examples of compounds in accordance with Formula I and Formula III are:

Pentyl (R)-2-(4-[4-(4-octyloxyphenyl)phenylcarbonyloxy]phenoxy)propanoate (POPOP), Methyl (R)-2-(4-[4-(4-octyloxyphenyl)phenylcarbonyloxy]phenoxy)propanoate (MOPOP), The compound of Formula I, in which n=1, may be prepared by reacting compound of the formula:

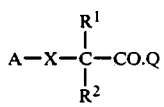

III wherein Q is OH or halogen, with an alcohol, Y—OH, viz.

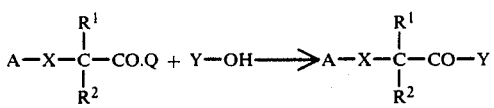

The compound of Formula III can itself be prepared by reacting an alpha-halocarboxylic acid of the formula:

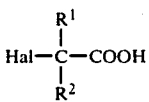

IV with a compound, A—X—H, capable of forming a charged species A—X⁻ which will displace the alpha-halogen atom on the carboxylic acid, viz.

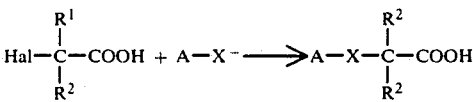

The acid can be used as such or converted into the acid chloride by known means, such as reaction with oxalyl chloride.

Examples of suitable compounds from which A—X⁻ is derivable are phenols (A—OH) and their thio (A—SH) analogues, such as:
4-phenylphenol
4-cyclohexylphenol
4-(bicyclo[2,2,2]oct-1-yl)phenol
4-(phenylcarbonyloxy)phenol
4-(2-phenylethyl)phenol
4-(cyclohexoxymethyl)phenol
4-(2-cyclohexoxyethyl)phenol
4-(phenylmethinazo)phenol
4-(4-octyloxyphenyl)phenol
4-(4-octylphenyl)phenol
4-(4-phenylphenylcarbonyloxy)phenol
4-(4-cyclohexylphenylcarbonyloxy)phenol
4-(2-[4-phenylcyclohexyl]ethyl)phenol
4-(4-[2-cyclohexylethyl]phenyl)phenol
4-(4-[2-phenylethyl]phenyl)phenol
4-[4-(2-[4-cyclohexylphenyl]ethyl)phenyl]phenol
4-[4-(2-[4-phenylcyclohexyl]ethyl)phenyl]phenol and
4-(4-phenylphenyl)phenol
and cyclo-alcohols or cyclic alkanols (A—OH) and their thio (A—SH) analogues, such as:
4-cyclohexylcyclohexanol
4-phenylcyclohexanol
4-(bicyclo[2,2,2]oct-1-yl)cyclohexanol
4-(1,3-dioxan-2-yl)cyclohexanol
4-(1,3-pyrimidin-2-yl)cyclohexanol
4-(2-phenylethyl)cyclohexanol
4-(phenylcarbonyloxy)cyclohexanol
4-(phenylmethinazo)cyclohexanol
4-(4-octylphenyl)cyclohexanol
4-(4-octyloxyphenyl)cyclohexanol
4-(4-phenylphenylcarbonyloxy)cyclohexanol
4-(4-cyclohexylphenylcarbonyloxy)cyclohexanol
4-(4-[2-cyclohexylethyl]phenyl)cyclohexanol
4-(4-[cyclohexoxymethyl]phenyl)cyclohexanol
4-(4-phenylphenyl)cyclohexanol
4-(4-[4-phenylphenylcarbonyloxy]phenyl)cyclohexanol
2-(2-cyclohexylethyl)-1,3-dioxan-4-ol and
4-(2-phenylethyl)bicyclo(2,2,2)octan-1-ol
any one of which may be, and preferably is, substituted in the 4-position on the terminal ring remote from the OH group by a group represented by R³, particularly where R³ is $C_{4-12}$-alkyl or alkoxy, and in any of the other positions by one or more of the groups listed above as substituents for the groups represented by A¹ to A⁴.

Alternatively, the compound of Formula I is derivable from a precursor of the compound, A—X—H, containing less than the required number of cyclic groups, A¹ to A⁴, which can be reacted with the alpha-halo- carboxylic in a similar manner and subsequently built up into the compound of Formula I by esterification and addition of further cyclic groups.

Thus a process for the preparation of a compound of Formula I wherein n=1 and A is a group of the formula:

$$R^3-(A^1)_i-T^1-(A^2)_j-T^2-(A^3)_k-T^3-A^4-$$  II wherein
R³ is selected from H, alkyl, alkoxy, alkylthio, fluoroalkyl & alkoxy, alkoxyalkyl, halogeno, alkyl- carbonyl & carbonyloxy and alkoxy- carbonyl & carbonyloxy;

T¹ & T² are independently selected from a single covalent bond or a group selected from —CO.O—, —O.CO—, —CO.S—, CS.O—, —CH=CH—, —CH₂O—, —OCH₂—, —N=N—,

—N=N—, —N=N—,
    |        |
    O        O

—N=CH—, —CH=N—, —CH₂CHD—, and —CHDCH₂—;

T³ is —CO.O—;

D is selected from H, cyano, halogen, CF₃ and CH₃;

A¹, A², A³ & A⁴ are independently selected from: optionally substituted 1,4-phenylene, optionally substituted 1,4-cyclohexylene optionally with one or two cyclic carbon atoms replaced by O or S, 1,4-bicyclo(2,2,2)octane, or 1,6-naphthylene or 1,4-naphthylene; and i, j & k independently represent 0 or 1;
may comprise reacting a compound, of the formula:

$$R^3-(A^1)_i-T^1-(A^2)_j-T^2-(A^3)_k-CO.Q \qquad V$$

wherein Q is OH or halogen with a compound of the formula:

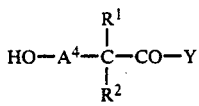  VI

An example of such a process is the formation of 2-(4-hydroxyphenoxy)propanoic acid by reaction of hydroquinone with 2-chloropropanoic acid, followed by esterification with pentan-1-ol, and conversion of the ester into a compound of Formula I, Pentyl (R)-2-(4-[4(4-octyloxyphenyl)phenylcarbonyloxy]phenoxy)-propanoate (POPOP), by reaction with 4-(4-octyloxyphenyl)benzoic acid (OPBA) or its acid chloride (OPBC).

The compound of Formula I, in which n=0, may be prepared by alkylating a substituted ethanoate of the formula:

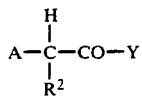  VII by reaction with an alkylating agent, $R^1X$, such as an alkyl halide, especially an iodide, in the presence of a strong base, such as lithium di-isopropylamide, sodamide or sodium hydride. Preferred groups represented by A in the compound of Formula VII are biphenyl, 4-cyclohexylphenyl, 4'-alkylbiphen-4-yl, 4'-alkoxybiphen-4-yl, 4-(2-[4'-alkylbiphen-4-yl]ethyl)phenyl and 4-(2-[4'-alkylbiphen-4-yl]methoxy)phenyl. This process is particularly appropriate where $R^2$ is H.

Alternatively the compound of Formula I in which n=0 can be prepared from a precursor of the ethanoate compound of Formula VII in which the group A is replaced by a smaller group comprising less than the desired number of cyclic groups, $A^1$ to $A^4$, and adding these latter groups after alkylation of the ethanoate. Thus, where $T^3$ is —CO.O— the compound of Formula I in which n=0 may be prepared by reaction of the compound:

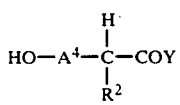  VIII with an alkylating agent ($R^1X$) in the presence of a strong base, after protection of the free OH group (e.g. with a trimethylsilyl group), to form the compound:

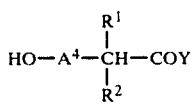  IX and then forming the compound of Formula I by removing the protection from the OH group and reacting this with a compound of Formula V. Variations in the value of Y can be obtained by transesterification of the compound of Formula VIII with a different alcohol, $Y^1$—OH.

An example of such a preparation is the formation of methyl 2-(4-hydroxyphenyl)propanoate by the reaction of a hydroxyl-protected methyl 2-(4-hydroxyphenyl)ethanoate, such as methyl 2-(4-[trimethylsilyloxy]-phenyl)ethanoate, with lithium di-isopropylamide and methyl iodide. This can then be either acylated with a 4-(4-alkyloxyphenyl)phenylcarbonyl chloride to give a methyl 2-(4-[4-(4-alkyloxyphenyl)phenylcarbonyloxy]-phenyl)propanoate or alternatively transesterified with another alcohol, such as ethanol, to give ethyl 2-(4-hydroxyphenyl)propanoate which can be acylated as before to give ethyl 2-(4-[4-(4-alkyloxyphenyl)phenyl-carbonyloxy]phenyl)propanoate.

Because they contain an asymmetric carbon (C*) the compounds of Formula I, in optically pure form, exhibit a large spontaneous polarisation ($P_s$) when the molecules are arranged in a tilted smectic mesophase. Furthermore, some of these compounds, particularly those of Formula III, also exhibit a tilted smectic mesophase, especially a smectic C mesophase, at temperatures close to ambient.

A compound of Formula I which exhibits both these properties can be used as the active ingredient in a device, employing the ferroelectric effect for the modulation of electromagnetic radiation, which is operational at or close to ambient temperature. Compounds of Formula I which do not exhibit a tilted smectic mesophase over a convenient temperature range can be used in a similar manner if they are formulated into a composition with a second compound which does exhibit the desired tilted smectic mesophase in a convenient temperature range. In such a composition the compound of Formula I provides the large spontaneous polarisation and the second compound orientates it in a tilted mesophase.

The invention is further illustrated by the following examples in which all parts and percentages are by weight unless otherwise indicated. In the Examples SOR is the specific optical rotation, $[\alpha]_{589}^T$, at 589 nm and ambient temperature (T=20°–25° C.) in chloroform.

EXAMPLE 1

(a) Pentyl (R)-2-(4-hydroxyphenoxy)propanoate (PHPP)

A mixture of the (R)-2-(4-hydroxyphenoxy)propionic acid (11 mmole) in toluene (30 ml), 1-pentanol (30 mmole), 98% $H_2SO_4$ (0.2 ml) and boric acid (0.1 g) was heated to reflux and water removed by azeotropic distillation on a Dean & Stark apparatus. After 3 hours the excess toluene was allowed to distil. The residue was allowed to cool and diluted with dichloromethane, washed with dilue HCl, water and saturated $NaHCO_3$ solution, dried ($MgSO_4$) and the crude product isolated by evaporation. This was distilled (Kugelrohr b.p. 150°–60° C. at 0.05 mbar) to give PHPP (yield 57%).

(b) 4-[4-Octyloxyphenyl]benzoyl Chloride (OPBC)

4-[4-Octyloxyphenyl]benzoic acid (OPBA) was converted into its acid chloride, OPBC, by heating it at reflux with oxalyl chloride after which excess oxalyl chloride was allowed to distil out and the residue taken up in ethanol free chloroform.

(c) Pentyl (R)-2-(4-[4-(4-octyloxyphenyl)benzoyloxy]phenoxy)-propanoate (POPOP)

PHPP (4.0 mmole), from Example 1(a), in dry ethanol free chloroform (5 ml) was added to the chloroform solution of OPBC (4 mmole) from Example 1(b), followed by dry pyridine (11 mmole). The mixture was heated at 60° C. for 16 hours, cooled to room temperature and diluted with dichloromethane. After washing with dilute HCl, water and a saturated solution of NaHCO$_3$, the mixture was dried (MgSO$_4$) and the crude product isolated by evaporation. This product was subjected to column chromatography (silica gel, eluent 2:1 hexane:chloroform to give a white solid that was recrystallised from hexane (yield 36%; mp 55° C.; SOR: +16°,c=15.6). The structure of the product, as POPOP, was confirmed by elemental analysis, IR, $^1$H-NMR and mass spectroscopy.

EXAMPLE 2

(a) (R)-2-(4-hydroxyphenylthio)propanoic acid (HPTPA)

To a solution of (S)-2-chloropropanoic acid (0.25 mole) in ethanol (500 ml/mole) and water (50 ml/mole) with sodium hydroxide (2.25 mole equiv) at 0° C. was added 4-hydroxyphenylthiol (0.18 mmole). The mixture was allowed to warm to room temperature slowly and then heated at 50°-60° C. for 1-4 hours. The cold solution was acidified with concentrated HCl to pH=1 and extracted with 4-methyl-2-pentanone or ethylacetate. The organic phase was dried (MgSO$_4$) and the crude product isolated by evaporation. The pure product was obtained by recrystallisation from chloroform or methanol to constant optical rotation (yield 79%; mp 138°-139° C.; SOR: +102°,c=2).

(b) Propyl (R)-2-(4-hydroxyphenylthio)propanoate (PHPTP)

A solution of HPTPA (0.06 mole, 11 g) in an molar excess of 1-propanol (45 ml), containing a crystal of p-toluene sulphonic acid, was heated at reflux while allowing water to distil from the reaction mix. When no acid remained, as shown by IR-spectroscopy, the excess solvent was allowed to distil out and the cold residue taken into ether and washed with saturated NaHCO$_3$ solution, dried (MgSO$_4$) and the crude product isolated by evaporation. This was purified by distillation under reduced pressure (yield: 83%; SOR: +98°,c=2). The properties of the product determined by IR, $^1$H-NMR and mass spectroscopy and elemental analysis were consistent with the assigned structure.

(c) Propyl (R)-2-[4-(4-[4-(octyloxyphenyl]phenylcarbonyloxy)-phenylthio]-propanoate (POPTP)

To OPBC (8.5 mmoles) in ethanol-free chloroform (1 ml/mole), prepared as in Example 1(b), was added PHPTP (9 mmole), prepared as in Example 2(b), and pyridine (20 mmole) and the mixture heated for 5 hours at reflux. The cooled reaction mix was diluted with dichloromethane and washed with dilute HCl, saturated NaHCO$_3$ and 1M NaOH solutions, stirred over activated charcoal, dried and the crude product isolated by evaporation. This was purified by column chromatography (silica gel; eluant: hexane-dichloromethane) and recrystallised from ethanol or chloroform-hexane (yield 93%; SOR +57°).

EXAMPLE 3

(a) (R)-2-(4-hydroxyphenoxy)propanoic acid (HPOPA)

This was prepared by the same method as HPTPA (Example 2a) using an equivalent amount of 4-hydroxyphenol in place of the 4-hydroxyphenylthiol used in Example 2(a) (yield 70%).

(b) Methyl (R)-2-(4-hydroxyphenoxy)propanoate (MHPOP)

To a mixture of (R)-2-(hydroxyphenoxuy)propanoic acid (0.15 mole) in 2,2-dimethoxypropane (0.2 mole) was added conc-HCl (0.5 ml). After stirring for 4 hours the reaction mixture was diluted with dichloromethane, washed with satureated-NaHCO$_3$, stirred with activated charcoal, dried and the solvent removed. The residual brown oil was distilled to give MHPOP (yield 56%; SOR +40°,c=10). The results of IR, $^1$H-NMR, mass spectroscopy and elemental analysis were consistent with the assigned structure.

(c) Methyl (R)-2-(4-[4-(4-octyloxyphenyl)phenylcarbonyloxy]-phenyoxy)propanoate (MOPOP)

This was prepared by the method used for POPTP (Example 2c) using an equivalent amount of MHPOP in place of the PHPTP used in Example 2(c) (yield: 82%; SOR: +17.8°,c=10). The results of IR, $^1$H-NMR, mass spectroscopy and elemental analysis were consistent with the assigned structure.

EXAMPLE 4

(a) (R)-2-(2/3-fluoro-4-hydroxyphenoxy)propanoic acid (2/3FHPOPA)

This was prepared by the same method as HPTPA (Example 2a) using an equivalent amount of 3-fluoro-4-hydroxyphenol in place of the 4-hydroxyphenylthiol used in Example 2(a) except that the recrystallisation was omitted. The product comprised a mixture of 2-fluoro, 3-fluoro isomers.

(b) Methyl (R)-2-(2-fluoro-4-hydroxyphenoxy)propanoate (M2FHPOP)

(b') Methyl (R)-2-(3-fluoro-4-hydroxyphenoxy)propanoate (M3FHPOP)

A mixture of these isomers, M2/3FHPOP, was prepared by the same method as PHPTP (Example 3b) using an equivalent amount of 2/3FHPOPA in place of the HPOPA used in Example 3(b). M2FHPOP (SOR: 38°,c=3) and M3FHPOP (SOR: 54°,c=9) were separated by column chromatography (silica gel, eluted with hexane-chloroform). The results of IR, $^1$H-NMR and mass spectroscopy and elemental analysis of the two products were consistent with the assigned structures.

(c) Methyl (R) 2-[2-fluoro-4-(4-[4-(octyloxyphenyl]phenylcarbonyloxy)phenoxy]-propanoate (M2FOPOP)

This was prepared by the method used for POPTP (Example 2c) using an equivalent amount of P2FHPOP in place of the PHPTP used in Example 2(c) (yield:

32%; SOR: +25°). The results of IR, $^1$H-NMR and mass spectroscopy and elemental analysis were consistent with the assigned structure.

(d) Methyl (R)-2-[3-fluoro-4-(4-[4-(octyloxyphenyl]phenylcarbonyloxy)phenoxy]-propanoate (M3FOPOP)

This was prepared in an exactly analogous manner to P2FOPOP (yield 44%; SOR: +17°). The results of IR, $^1$H-NMR and mass spectroscopy and elemental analysis were consistent with the assigned structure.

EXAMPLE 5

(a) Hexyl (R)-2-[2-fluoro-4-(4-[4-(octyloxyphenyl]phenylcarbonyloxy)phenoxy]-propanoate (H2FOPOP)

This was prepared by the method used for M2FOPOP (Example 4b and 4c) using an equivalent amount of n-hexanol in place of the dimethanoxypropane used in Example 4(b) (yield: 47%; SOR: +23°). The results of IR, $^1$H-NMR and mass spectroscopy and elemental analysis were consistent with the assigned structure.

(b) Hexyl (R)-2-[3-fluoro-4-(4-[4-(octyloxyphenyl]phenylcarbonyloxy)phenoxy]-propanoate (H3FOPOP)

This was prepared in an exactly analogous manner to M3FOPOP (Example 4b and 4d) using an equivalent amount of n-hexanol in place of the dimethanoxypropane used in Example 4(b) (yield 28%; SOR: +17°). The results of IR, $^1$H-NMR and mass spectroscopy and elemental analysis were consistent with the assigned structure.

EXAMPLES 6 to 13

Six compounds of the following formula:

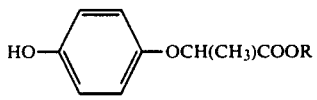

were prepared from HPOPA by the general method of Example 2(b), in each case using an alcohol, ROH, in place of the propanol used in Example 2(b) and giving the product indicated, with yield and SOR, in Table 1. For each compound the results of IR, $^1$H-NMR and mass spectroscopy and elemental analysis were consistent with the assigned structure.

TABLE 1

| Example | R | Yield | SOR (c=) |
|---|---|---|---|
| 6(a) | ethyl | 98% | +43 (10) |
| 7(a) | propyl | 94% | +41 (3) |
| 8(a) | butyl | 34% | +43 (7) |
| 9(a) | hexyl | 92% | +37 (4) |
| 10(a) | octyl | 91% | +32 (3) |
| 11(a) | dodecyl | 93% | +13 (2) |
| 12(a) | 2-ethylbutyl | 68% | +42 (3) |

The six compounds of the following formula:

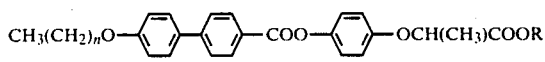

were prepared from Examples 6(a) to 12(a) by the general method of Example 3(c), in each case using an acid chloride of the following formula:

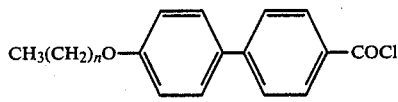

to give the product indicated, with yield and SOR, in Table 2. For each compound the results of IR, $^1$H-NMR and mass spectroscopy and elemental analysis were consistent with the assigned structure.

TABLE 2

| Example | R | n | Yield | SOR | (c=) |
|---|---|---|---|---|---|
| 6(b) | ethyl | 7 | 65% | +19° | (4) |
| 7(b) | propyl | 7 | 88% | +19° | (4) |
| 8(b) | butyl | 7 | 44% | +19° | (4) |
| 9(b) | hexyl | 7 | 45% | +19° | (4) |
| 9(c) | hexyl | 10 | 37% | +8° | (4) |
| 9(d) | hexyl | 5 | 62% | +19° | (1.5) |
| 10(b) | octyl | 7 | 60% | +18° | (1) |
| 11(b) | dodecyl | 5 | 37% | +16° | (4) |
| 12(b) | 2-ethylbutyl | 7 | 61% | +20° | (1.5) |

EXAMPLE 13

Butyl (R)-2-(4-[4-(3-chloro-4-octyloxyphenyl)phenylcarbonyloxy]phenoxy)propanoate (BCOPOP)

This was prepared by the methods of Examples 2(b) and 2(c) using butanol instead of propanol and using 4-(3-chloro-4-octoxyphenyl)benzoyl chloride and Butyl (R)-2-(4-hydroxyphenoxy)propanoate (BHPP) in place of the OPBC and PHPTB used in Example 2(c), (yield 15%, SOR: +16°). The results of IR, $^1$H-NMR and mass spectroscopy and elemental analysis were consistent with the assigned structure.

EXAMPLE 14

Propyl (R)-2-(4-[3-fluoro-4-(4-octyloxyphenyl)phenylcarbonyloxy]phenoxy)propanoate (PFOPOP)

This was prepared by the methods of Examples 2(b) and 2(c) using 3-fluoro-4-(4-octoxyphenyl)benzoyl chloride in place of the OPBC used in Example 2(c), (yield 30%, SOR: +18°). The results of IR, $^1$H-NMR and mass spectroscopy and elemental analysis were consistent with the assigned structure.

EXAMPLE 15

Hexyl (R)-2-(4-[4-(t-4-heptylcyclohexyl)phenylcarbonyloxy]-phenoxy)propanoate (HHCPP)

This was prepared by the method of Example 2(b) and 2(c) using hexanol in place of propanol and 4-(t-4-heptylcyclohexyl)benzoyl chloride in place of OPBC to give HHCPP (yield 48%; SOR: +20°). The results of IR, $^1$H-NMR and mass spectroscopy and elemental analysis were consistent with the assigned structure.

EXAMPLE 16

Hexyl (R)-2-[4-(4-[4-nonylphenyl]phenylcarbonyloxy)-phenyoxy]propanoate (HNCPP)

This was prepared by the method of Example 2(b) and 2(c) using hexanol in place of propanol and 4-(4-nonylphenyl)benzoyl chloride in place of OPBC to give HNCPP (yield 37%; SOR: +19°). The results of IR, $^1$H-NMR and mass spectroscopy and elemental analysis were consistent with the assigned structure.

EXAMPLE 17

(a) Hexyl (R)-2-(4-formylphenoxy)propanoate (HFPP)

Sodium hydride (0.4 mole) was suspended in dimethyl formamide (20 ml). 4-Hydroxybenzaldehyde (0.2 mole) in DMF (50 ml) was added. After the effervesence had subsided, 2-chloropropanoic acid (0.22 mole) was added dropwise. During the addition the reaction temperature rose to 70° C. The mixture was stirred overnight at 110° C. Upon cooling the mixture was diluted with saturated NaHCO$_3$ solution and extracted with ethyl acetate (3×100 ml). The aqueous phase was then acidified with concentrated HCl solution and extracted with ethyl acetate. After washing the second organic extract with water and evaporation, a brown oil was obtained. Crystallisation from hot chloroform and hexane gave a brown solid (7.6 g). The mother liquors were evaporated to dryness to yield a brown solid (17.3 g) used without further purification. (Total yield 64%). $^1$H-NMR spectroscopy showed these products to be greater than 90% pure (m.p. 114°-8° C.).

(b) Hexyl (R)-2-[4-(5-nonyl-1,3-dioxin-2-yl)phenoxy]propanoate (HNDPP)

A mixture of 2-hydroxymethyl-1-undecanol (10 mmole) HFPP (10 mmole) and p-toluenesulphonic acid (50 mg) in toluene (50 ml) was heated at reflux while allowing water to distil out. When reaction was complete the excess toluene was removed by distillation and the product allowed to cool before dilution with dichloromethane. After washing with saturated NaHCO$_3$ solution the mixture was distilled to give a colourless liquid identified as NDPP by IR, $^1$H NMR and mass spectroscopy and elemental analysis (yield: 68%; bp: 230°-40° C. at 0.3 mbar; SOR: 5.9,c=3). The product was a 85:15 mixture of the trans and cis isomers.

EXAMPLE 18

Hexyl (R)-2-(4-[4-(4-nonyphenyl)phenylmethoxy]phenoxy)-propanoate (HNMPP)

4-(4-Nonylphenyl)phenylbromide (4.5 mmole), the product of Example 9(a) (5 mmole) and NaH$_2$ (4.5 mmole) in N,N-dimethylformamide (10 ml) were stirred overnight at ambient temperature. The turbid mixture was diluted with dichloromethane and washed with dilute HCl and saturated NaHCO$_3$. The excess solvent was removed under reduced pressure and the residue purified by column chromatography (silica gel; eluant dichloromethane/hexane) to give HNMPP (72%; SOR: +20°,c=1.4). The results of IR, $^1$H-NMR and mass spectroscopy and elemental analysis were consistent with the assigned structure.

EXAMPLE 19

Hexyl (R)-2-(4-[2-(4-[4-nonylphenyl]phenyl)-eth-1-yl]phenoxy)propanoate (HNPPP)

4-(4-Nonylphenyl)phenylmethyl-triphenylphosphonium bromide (5 mmole) was suspended in dry toluene (30 ml). A solution of butyl-lithium (5 mmole, 1.2M in hexane) was added dropwise at room temperature. To the resulting orange solution was added HFPP (see Example 18a; 5 mmole) in dry toluene (1 ml). After stirring for 1 hour at room temperature and for 30 minutes at 60° C., the cooled mixture was diluted with dichloromethane, washed with dilute HCl and saturated NaHCO$_3$, dried (MgSO$_4$) and the product isolated by evaporation. Column chromatography (silica gel eluted with hexane-chloroform) of this gave a white solid, identified by $^1$H-NMR spectroscopy as a mixture of cis and trans stilbenes. The mixture was used without further purification in the next stage.

The mixture (0.9 g) in ethylacetate (20 ml) with 10% Pd/C (20 mg) was stirred at room temperature under an atmosphere of hydrogen. After 30 hours the catalyst was removed by filtration and the solvent evaporated. Column chromatography of the residue followed by recrystallisation from ethanol gave white needles of HNPPP (yield 29%; SOR: +5°,c=1.7).

EXAMPLE 20

(a) Preparation of Methyl 2-(4'-hydroxyphenyl)propanoate (MHPP)

Under an atmosphere of nitrogen, diisopropylamine (39 mmole) in dimethoxyethane at −30° C. was treated with n-butyl-lithium (1.2M in hexane, 36 mmole). The temperature was allowed to rise to 0° C. and then cooled to −70° C.

A solution of methyl 2-(4'-trimethylsilyloxyphenyl)ethanoate (34.3 mmole) in dimethoxyethane (10 ml) was added dropwise to the reaction, the temperature rising to −30° C. before cooling to −70° C. This cold reaction mix was added dropwise to a solution of methyliodide (0.16 mole) in dimethoxyethane (20 ml) cooled to −70° C. The mixture was stirred at room temperature overnight before removing the solvent by evaporation. The residue was stirred with dilute HCl and extracted with dichloromethane, washed with saturated NaHCO$_3$ solution, dried (MgSO$_4$) and the product isolated by evaporation. Distillation of the crude product gave MHPP (yield 88%).

(b) (S)-2-Methylbutyl 2-(4-hydroxyphenyl)propanoate (MBHP)

A mixture of MHPP (2.0 g, 12 mmole) and tetra-(n-butyl)titanate (2 drops) in (S)-2-methylbutanol (5 ml) was stirred at reflux for 16 hours after which excess alcohol was allowed to distill, out and the residual product recovered by distillation (yield 90%; bp 155°-60° C.; SOR: +5.4°,c=3). The results of IR, $^1$H-NMR and mass spectroscopy and elemental analysis were consistent with the assigned structure.

(c) (S)-2-Methylbutyl 2-(4-[4-(4-octyloxyphenyl)phenylcarbonyloxy]phenyl)-propanoate This prepared by the method of Example 2(d), at 4.2 mmole scale) using an equivalent amount of MBHP in place of PHPTP (yield 48%; SOR +14°,c=9). The

(d) Methyl 2-(4-[4-(4-octyloxyphenyl)phenylcarbonyloxy]phenyl)-propanoate (MOPPP)

This was prepared by the same method as Example 20(c) at the 5 mmol scale using MHPP from Example 20(a) in place of the MBHP to give MOPPP (yield 41%). The results of IR, $^1$H-NMR and mass spectroscopy and elemental analysis were consistent with the assigned structure.

EXAMPLES 21 to 23

Compounds having the general formula:

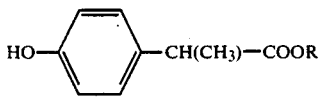

were prepared from MHPP by the method of Example 20(b) at the scale (mmole) indicated in Table 3, in each case using an alcohol, R—OH, in place of the (S)-2-methylbutanol used in Example 20(b) and giving the product with the yield indicated in Table 3.

TABLE 3

| Example | R | Scale | Yield |
| --- | --- | --- | --- |
| 21(a) | n-propyl | 7.2 | 80% |
| 22(a) | n-butyl | 5.0 | 94% |
| 23(a) | n-pentyl | 3.6 | 75% |

Compounds of the general formula:

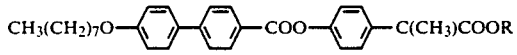

were prepared from Examples 21(a) to 23(a) by the method of Example 2(c) at the scale indicated in Table 4, in each case using OPBC to give the product indicated with yield in Table 4. In each case, the results of IR, $^1$H-NMR and mass spectroscopy and elemental analysis were consistent with the assigned structure.

TABLE 4

| Example | R | Scale | Yield |
| --- | --- | --- | --- |
| 21(b) | n-propyl | 4.8 | 45% |
| 22(b) | n-butyl | 4.5 | 20% |
| 23(b) | n-pentyl | 3.6 | 33% |

EXAMPLE 24

Methyl 2-bromo-2-(4-[4-(4-octyloxyphenyl)phenylcarbonyloxy]phenyl)propanoate (MBOPP)

A mixture of MOPPP (see Example 20d; 1.1 mmole) in dry CCl$_4$ (10 ml) with N-bromosuccinimide (1.8 mmole) and a catalytic quantity of azo-isobutyronitril (5 mg) was heated for 24 hours. After cooling, the reaction mixture was purified directly by column chromatography (silica gel eluted with hexane/chloroform). MBOPP was recrystallised from hexane as fine needles (yield 45%; mp 104°-5° C.). The results of IR, $^1$H-NMR and mass spectroscopy and elemental analysis were consistent with the assigned structure.

PROPERTIES OF COMPOUNDS OF FORMULA I PREPARED IN THE EXAMPLES

The Test Cells and Filling Procedure

The compounds of Formula I were assessed for their phase and electro-optic properties in standard cells comprising parallel plane glass ends of 0.7 mm soda-lime glass spaced by chopped optical glass fibres with a single filling hole. The internal area of each face was 12 mm by 12 mm and cell thickness is 5 μm, 8 μm or 14 μm. A 5 mm by 5 mm electrode area was formed on the internal face of each face end by patterned ITO. Electric connections to the cell were made through electrodes soldered to the edge of the cell.

The cells were filled under vacuum and the filling port then sealed to avoid contamination.

Alignment of Molecules

Uniform, unidirectional planar alignment of the molecules in the semectic C phase was achieved by the method of J. Patel and J. W. Goodby (see J. Appl. Phys. 59, 7 (1986).

Phase Properties

These were determined by classical microscopic techniques (see "Textures of Liquid Crystals" by Demus & Richter, Verlag Chemie, 1978) using an electric field to show up ferroelectric phases. The results are set out in Table 5 below.

Ferroelectric Properties

The ferroelectric properties measured were (a) Spontaneous Polarisation ($P_s$), (b) Tilt Angle and (c) Response Time (the time to switch from one tilted phase to the other). The ferroelectric properties of the exemplified compounds are set out in Table 6 below.

(a) Spontaneous Polarisation

This was determined by the method of Sawyer and Tower (see Phys. Rev. 35, 269, 1930) and Diament et al (see Rev. Sci. Inst., 28, 30, 1957).

(b) Tilt Angle

To a test cell containing a sample of the LC material which had been aligned as hereinbefore described, was applied an electric field of sufficient magnitude to fully unwind the molecule from its normal helical form (about 2 v across 8 μm cell). The direction of tilt was determined by rotation of the cell between crossed polarised layers until extinction was obtained. The other direction of tilt was determined by reversing the polarity of the electric field and repeating the rotation until extinction was again obtained. The title angle is the angle of rotation of the cell between the two extinction positions.

(c) Response Time

Response time is determined by aligning the molecules in one of the tilted smectic C phases and aligning a polariser so that a beam of light passing through the cell is at a maximum. the electric field is then switched to the opposite polarity causing the molecules to flip into the other tilted phase and altering the amount of light passing through the cell. The electric field switch is coupled to a photodiode which records the time taken for the change in transmitted light to take place.

TABLE 5

| Example | M.P. | Phase Properties — Mesophases & Transition Temperatures |
|---|---|---|
| 1(c) | 65° C. | $S_I$ —48° C.— $S_C$ —58° C.— $S_A$ —111° C.— I |
| 2(c) | 64° C. | $S_X$ —50° C.— $S_C$ —71° C.— $S_A$ —120° C.— I |
| 3(c) | 95° C. | $S_I$ —80° C.— $S_C$ —111° C.— $S_A$ —145° C.— I |
| 4(c) | 80° C. | $S_C$ —104° C.— $S_A$ —141° C.— I |
| 4(d) | 78° C. | $S_X$ —————— $S_A$ —108° C.— Ch —111° C.— I |
| 5(a) | — | $S_C$ —55° C.— $S_A$ —107° C.— I |
| 5(b) | 38° C. | $S_A$ —60° C.— Ch —76° C.— I |
| 6(b) | 75° C. | $S_C$ —93° C.— $S_A$ —134° C.— I |
| 7(b) | 62° C. | $S_X$ —65° C.— $S_C$ —83° C.— $S_A$ —132° C.— I |
| 8(b) | 65° C. | $S_X$ —69° C.— $S_C$ —78° C.— $S_A$ —117° C.— I |
| 9(b) | 53° C. | $S_C$ —46° C.— $S_A$ —109° C.— I |
| 9(c) | 53° C. | $S_C$ —71° C.— $S_A$ —103° C.— I |
| 9(d) | <20° C. | $S_X$ —59° C.—————— $S_A$ —113° C.— I |
| 10(b) | 46° C. | $S_C$ —43° C.— $S_A$ —105° C.— I |
| 11(b) | 64° C. | $S_X$ —36° C.—————— $S_A$ —104° C.— I |
| 12(b) | 48° C. | $S_C$ —73° C.— $S_A$ —95° C.— I |
| 13 | — | $S_C$ —26° C.— $S_A$ —46° C.— Ch —55° C.— I |
| 14 | 55° C. | $S_X$ —67° C.—————————— Ch —74° C.— I |
| 15 | 55° C. | $S_A$ —46° C.— Ch —64° C.— I |
| 16 | 10° C. | $S_A$ —75° C.— I |
| 17(b) | | Isotropic |
| 18 | 42° C. | $S_C$ —54° C.— I |
| 19 | — | $S_B$ —40° C.— I |
| 20(c) | 70° C. | $S_I$ —39° C.— $S_C$ —69° C.— $S_A$ —94° C.— I |
| 20(d) | 98° C. | $S_I$ —64° C.— $S_C$ —94° C.— $S_A$ —128° C.— I |
| 21(b) | 50° C. | $S_I$ —47° C.— $S_C$ —74° C.— $S_A$ —107° C.— I |
| 22(b) | 56° C. | $S_I$ —41° C.— $S_C$ —66° C.— $S_A$ —104° C.— I |
| 23(b) | 58° C. | $S_I$ —36° C.— $S_C$ —57° C.— $S_A$ —101° C.— I |
| 24 | 100° C. | $S_C$ —70° C.— $S_A$ —101° C.— I |

TABLE 6

| | Electro-Optic Properties | | | | |
|---|---|---|---|---|---|
| | $P_s$ | | Tilt Angle | Response Time | |
| Example | (nC/cm$^2$) | at | (°) at | (ms) | at |
| 1(c) | 184 | 35° C. | 17.5 35° C. | 0.1 | 50° C. |
| 3(c) | 154 | 64° C. | — — | — | — |
| 4(c) | 275 | 40° C. | — — | 0.25 | 70° C. |
| 5(a) | 230 | 26° C. | 20.0 26° C. | 1.0 | 26° C. |
| 6(b) | 185 | 55° C. | — — | — | — |
| 7(b) | 195 | 45° C. | — — | — | — |
| 8(b) | 205 | 40° C. | — — | 2.0 | 51° C. |
| 9(b) | 176 | 30° C. | — — | 1.0 | 42° C. |
| 9(c) | 120 | 46° C. | 30.0 46° C. | — | — |
| 10(b) | 95 | 25° C. | 10.0 25° C. | — | — |
| 12(b) | 257 | 35° C. | 25.0 40° C. | 0.01 | 73° C. |
| 13 | 132 | 13° C. | — — | — | — |

I claim:

1. A ferroelectric liquid crystal material having the formula:

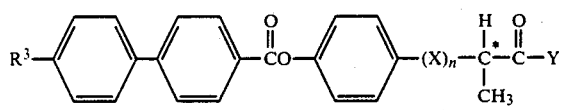

wherein
x represents an oxygen or sulphur atom;
n is 0 or 1;
R$^3$ represents an alkoxy group having from 4 to 12 carbon atoms in the alkyl group;
Y represents an alkoxy group having from 1 to 12 carbon atoms in the alkyl group; and
wherein one or more of the 1,4-phenylene rings can optionally carry up to four halogen substituents.

2. A ferroelectric liquid crystal material as claimed in claim 1 where one or more of the 1,4-phenylene rings carries a single halogen substituent.

3. A ferroelectric liquid crystal material as claimed in claim 1 wherein the halogen substituent(s) is a fluorine atom.

4. A ferroelectric liquid crystal material as claimed in claim 1 wherein n is 1.

5. A ferroelectric liquid crystal material as claimed in claim 4 wherein X is oxygen.

6. A ferroelectric liquid crystal material as claimed in claim 1 wherein R$^3$ represents an alkoxy group having from 5 to 12 carbon atoms in the alkyl group.

7. A ferroelectric liquid crystal material as claimed in claim 1 wherein R$^3$ represents an alkoxy group having from 6 to 12 carbon atoms in the alkyl group.

8. A ferroelectric liquid crystal material as claimed in claim 1 wherein Y represents an alkoxy group having from 4 to 12 carbon atoms in the alkyl group.

9. A ferroelectric liquid crystal material as claimed in claim 1, wherein the alkyl group contained in the alkoxy group represented by Y is a straight chain alkyl group.

10. A ferroelectric liquid crystal material as claimed in claim 1, wherein the alkyl group contained in the alkoxy group represented by Y is a branched alkyl group.

11. A ferroelectric liquid crystal material as claimed in claim 1 having the formula:

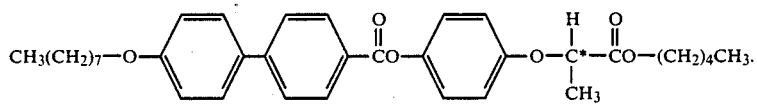

12. A ferroelectric liquid crystal material as claimed in claim 1 having the formula:

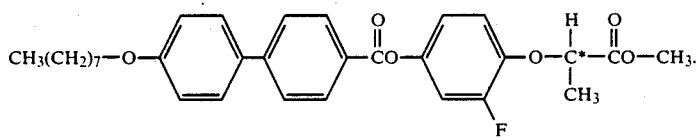

13. A ferroelectric liquid crystal material as claimed in claim 1 having the formula:

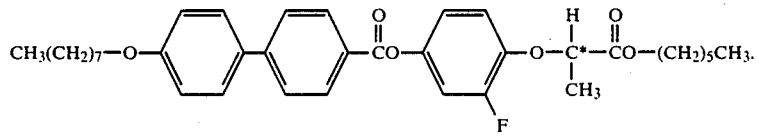

14. A ferroelectric liquid crystal material as claimed in claim 1 having the formula:

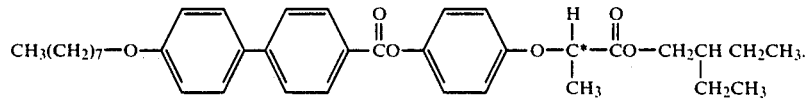

15. A device employing the ferroelectric effect for the modulation of electromagnetic radiation comprising a ferroelectric liquid crystal material according to claim 1.

* * * * *